United States Patent [19]

Elbe et al.

[11] Patent Number: 4,894,382

[45] Date of Patent: Jan. 16, 1990

[54] SUBSTITUTED 1,3-DIAZOLYL-2-PROPANOLS AND THEIR USE AS ANTIMYCOTIC AGENTS

[75] Inventors: Hans-Ludwig Elbe; Graham Holmwood; Erik Regel, all of Wuppertal; Karl H. Büchel, Burscheid; Klaus Schaller, Wuppertal; Manfred Plempel, Haan, all of Fed. Rep. of Germany

[73] Assignee: Bayer Aktiengesellschaft, Leverkusen, Fed. Rep. of Germany

[21] Appl. No.: 924,658

[22] Filed: Oct. 29, 1986

Related U.S. Application Data

[63] Continuation of Ser. No. 578,237, Feb. 8, 1984, abandoned.

[30] Foreign Application Priority Data

Mar. 2, 1983 [DE] Fed. Rep. of Germany ....... 3307217

[51] Int. Cl.$^4$ .................. A61K 31/415; A61K 31/41; C07D 249/08; C07D 403/06
[52] U.S. Cl. .................................. 514/383; 514/397; 548/262; 548/336
[58] Field of Search ................ 548/262, 336; 514/383, 514/397

[56] References Cited

U.S. PATENT DOCUMENTS

| | | | |
|---|---|---|---|
| 4,416,682 | 11/1983 | Worthington | 71/76 |
| 4,621,095 | 11/1986 | Regel et al. | 548/262 |
| 4,652,579 | 3/1987 | Holmwood et al. | 514/383 |
| 4,734,126 | 3/1988 | Holmwood et al. | 514/383 |

FOREIGN PATENT DOCUMENTS

| | | | |
|---|---|---|---|
| 0040345 | 11/1981 | European Pat. Off. | 548/262 |
| 0061835 | 10/1982 | European Pat. Off. | 548/262 |
| 3018865 | 11/1981 | Fed. Rep. of Germany | 424/269 |
| 2103210 | 2/1983 | United Kingdom | 548/262 |

*Primary Examiner*—Richard L. Raymond
*Assistant Examiner*—Patricia L. Morris
*Attorney, Agent, or Firm*—Sprung Horn Kramer & Woods

[57] ABSTRACT

The invention provides substituted 1,3-diazolyl-2-propanols defined herein generically by formula (I), useful as antimycotic agents. Also included in the invention are methods for the procurement of said substituted 1,3-diazolyl-2-propanols, compositions containing said antimycotic compounds and methods for the use of said compounds and compositions for treatment of mycoses.

16 Claims, No Drawings

SUBSTITUTED 1,3-DIAZOLYL-2-PROPANOLS AND THEIR USE AS ANTIMYCOTIC AGENTS

This is a continuation of application Ser. No. 578,237, filed 2/8/84, now abandoned.

The present invention relates to new substituted 1,3-diazolyl-2-propanols, a process for their preparation and their use as antimycotics.

It has already been disclosed that certain diazolyl derivatives have antimycotic properties.

New substituted 1,3-diazolyl-2-propanols of the formula

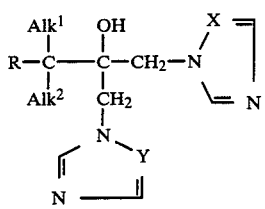

in which
Alk¹ represents straight-chain or branched alkyl and
Alk² represents straight-chain or branched alkyl, or
Alk¹ and Alk² together represent a cycloaliphatic ring,
X represents a nitrogen atom or the CH group,
Y represents a nitrogen atom or the CH group and
R represents in each case optionally substituted phenyl, phenylalkyl, phenoxy, phenylthio, phenoxyalkyl, phenylthioalkyl, benzyloxy or benzylthio, and physiologically acceptable acid addition salts thereof, have been found.

It has furthermore been found that the substituted 1,3-diazolyl-2-propanols of the formula (I) are obtained by a process in which 2-azolylmethyl-oxiranes of the formula

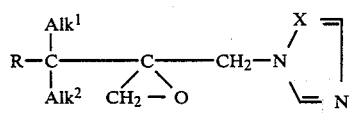

in which
Alk¹, Alk², R and X have the abovementioned meaning, are reacted with azoles of the formula

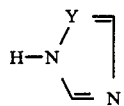

in which
Y has the abovementioned meaning, in the presence of a diluent and, if appropriate, in the presence of a base.

If appropriate, an acid can then be added onto the compounds of the formula (I) thus obtained.

The new substituted 1,3-diazolyl-2-propanols of the formula (I) have powerful antimycotic properties.

In addition, the new substituted 1,3-diazolyl-2-propanols are interesting intermediates.

Thus, for example, the compounds of the formula (I) can be converted into the corresponding ethers on the hydroxyl group in the customary manner. Furthermore, acyl or carbamoyl derivatives of the compounds of the formula (I) can be obtained by reaction with, for example, acyl halides or carbamoyl chlorides in a manner which is known in principle. These derivatives have the same antimycotic properties as the hydroxy compounds.

Moreover, the compounds of the formula (I) in which R represents in each case optionally substituted phenylthio, phenylthioalkyl or benzylthio can be oxidised to the corresponding SO or SO₂ derivatives in the customery manner. They have antimycotic properties, too.

Formula (I) provides a general definition of the substituted 1,3-diazolyl-2-propanols according to the invention. Preferably, in this formula Alk¹ represents straight-chain or branched alkyl with 1 to 3 carbon atoms; and Alk² represents straight-chain or branched alkyl with 1 to 3 or 4 carbon atoms; or Alk¹ and Alk² together represent a 3-membered to 7-membered cycloaliphatic ring, X represents a nitrogen atom or the CH group; Y represents a nitrogen atom or the CH group; and R represents phenyl, phenylalkyl with 1 to 4 carbon atoms in the alkyl part, phenoxy, phenylthio, phenoxyalkyl with 1 to 4 carbon atoms in the alkyl part, phenylthioalkyl with 1 to 4 carbon atoms in the alkyl part, benzyloxy or benzylthio, each of which is optionally mono-, di- or tri-substituted in the phenyl part by identical or different substituents, preferred substituents which may be mentioned being: halogen, alkyl with 1 to 4 carbon atoms, alkoxy and alkylthio with in each case 1 to 4 carbon atoms, halogenoalkyl, halogenoalkoxy and halogenoalkylthio with in each case 1 or 2 carbon atoms and 1 to 5 identical or different halogen atoms, such as, preferably, fluorine and chlorine atoms, nitro, cyano, hydroxyl, hydroxycarbonyl, alkoxycarbonyl with 1 to 4 carbon atoms in the alkyl part, hydroxyiminoalkyl or alkoxyiminoalkyl with 1 to 4 carbon atoms in each alkyl part, and phenyl, phenoxy, benzyl and benzyloxy, each of which is optionally substituted by halogen and/or alkyl with 1 or 2 carbon atoms.

Particularly preferred compounds of the formula (I) are those
in which
Alk¹ represents methyl or ethyl; and
Alk² represents methyl or ethyl; or
Alk¹ and Alk², together with the carbon atom to which they are bonded, represent cyclobutyl, cyclopentyl or cyclohexyl, X represents a nitrogen atom or the CH group; Y represents a nitrogen atom or the CH group; and R represents phenyl, benzyl, phenethyl, phenoxy, phenylthio, phenoxymethyl, phenoxyethyl, phenylthiomethyl, phenylthioethyl, benzyloxy or benzylthio, each of which is optionally mono- or di-substituted in the phenyl part by identical or different substituents, substituents which may be mentioned being: fluorine, chlorine, bromine, methyl, isopropyl, tert.-butyl, methoxy, methylthio, trifluoromethyl, trifluoromethoxy, trifluoromethylthio, nitro, cyano, hydroxyl, hydroxycarbonyl, methoxycarbonyl, ethoxycarbonyl, hydroximinomethyl, 1-hydroximinoethyl, methoximinomethyl, 1-methoximinoethyl, and phenyl, phenoxy, benzyl and benzyloxy, each of which is optionally substituted by fluorine, chlorine or methyl. Addition products of acids and those substituted 1,3-diazolyl-2-propanols of the formula (I) in which the substituents Alk¹, Alk², X, Y and R have the meanings which have already been mentioned as preferred for these substituents are also preferred compounds according to the invention.

Preferred acids which can be added on include the hydrogen halide acids, such as, for example, hydrochloric acid and hydrobromic acid, in particular hydrochloric acid, and furthermore phosphoric acid, nitric acid, mono-functional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as p-toluenesulphonic acid and 1,5-naphthalenedisulphonic acid.

If, for example, 2-(2,4-dichlorophenyl-tert.-butyl-—2—(1,2,4-triazol-1-yl-methyl)-oxirane and 1,2,4-triazole are used as starting substances, the course of the process according to the invention can be represented by the following equation:

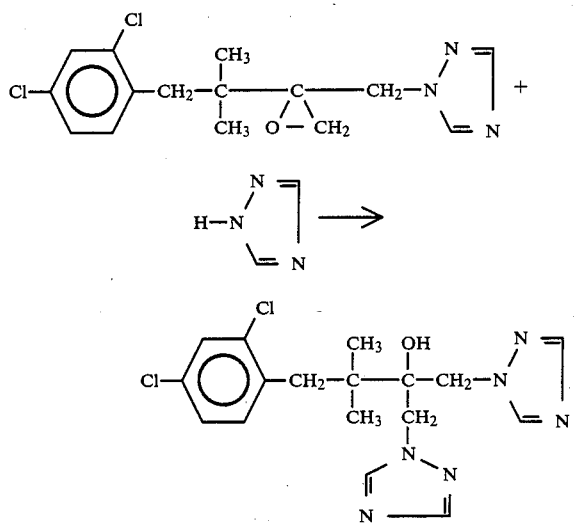

Formula (II) provides a general definition of the oxiranes to be used as starting substances for carrying out the process according to the invention. In this formula, Alk$^1$, Alk$^2$, R and X preferably have those meanings which have already been mentioned as preferred for these substituents in connection with the description of the substances of the formula (I) according to the invention.

The oxiranes of the formula (II) are known (compare DE-OS (German Published Specification) 3,111,238 corresponding to U.S. patent application Ser. No. 325,689 filed Feb. 26, 1982 now pending; or they are the subject of earlier applications which have been filed by the Applicant Company and have not yet been published (compare German Patent Applications P 32 02 601 of 1/22/82 and P 32 37 400 of 10/8/82); or they can be obtained in a generally known manner, by reacting azolyl-ketones of the formula

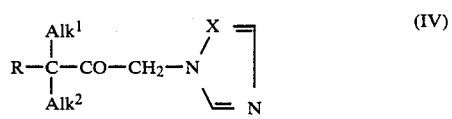

in which

Alk$^1$, Alk$^2$, R and X have the abovementioned meaning, either ($\alpha$) with dimethyloxosulphonium methylide of the formula

in a manner which is known per se in the presence of a diluent, such as, for example, dimethylsulphoxide, at temperatures between 20° C. and 80° C. (in this context, note J. Am. Chem. Soc. 87, 1363–1364 (1965)). or ($\beta$) with trmethylsulphonium methyl-sulphate of the formula

in a manner which is known per se, in the presence of an inert organic solvent, such as, for example, acetonitrile, and in the presence of a base, such as, for example, sodium methylate, at temperatures between 0° C. and 60° C., preferably at room temperature (note also Heterocycles 8, 397 (1977)).

If appropriate, the oxiranes of the formula (II) thus obtained can be further reacted directly, without being isolated.

The azolyl-ketones of the formula (IV) are known compare DE-OS (German Published Specification) 3,111,238, corresponding to U.S. patent application Ser. No. 352,689 filed 2/26/82, or they can be prepared by processes which are known in principle.

Formula (III) provides a general definition of the azoles also to be used as starting substances for the process according to the invention. In this formula, Y preferably has the meanings which have already been mentioned for this substituent in the definition of the invention.

Possible diluents for the process according to the invention are organic solvents which are inert under the reaction conditions, these include, preferably, alcohols, such as, C$_1$–C$_3$-alkanols or alkoxy alkanols, for example, ethanol, methoxyethanol or propanol; ketones, such as, C$_2$–C$_4$-alkyl ketones, for example, 2-butanone; nitriles, such as, for example, acetonitrile; esters, such as C$_1$–C$_4$-alkyl esters of C$_1$–C$_4$-alkane carboxylic acids such as, for example, ethyl acetate; ethers, such as, for example, dimethyl or diethyl ether dioxane; aromatic hydrocarbons, such as, for example, benzene and toluene; or amides, such as, for example, dimethylformamide.

Possible bases for the reaction according to the invention are all the inorganic and organic bases which can customarily be used. These include, preferably, alkali metal carbanates, such as, for example, sodium carbonate and potassium carbonate; alkali metal hydroxides, such as, for example, sodium hydroxide, ammonium bases, alkali metal alcoholates, such as, for example, sodium ethylate and ethylate and potassium ethylate and ethylate; alkali metal hydrides, such as, for example, sodium hydride; and lower tertiary alkylamines, cycloalkylamines and aralkylamines, such as, in particular, triethylamine.

The reaction temperatures can be varied within a substantial range in carrying out the process according to the invention. In general, the reaction for all reaction steps is carried out at temperatures between 0° C. and 200° C., preferably between 60° C. and 150° C.

In carrying out the process according to the invention, 1 to 2 moles of azole of the formula (III) and, if appropriate, 1 to 2 moles of base are preferably employed per mole of oxirane of the formula (II); the end products are isolated in the generally customary manner.

The compounds of the formula (I) can also be obtained by reacting diazolyl-ketones of the formula

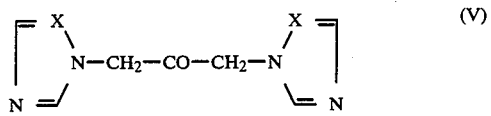

in which

X and Y have the abovementioned meaning, with a Grignard reagent of the formula

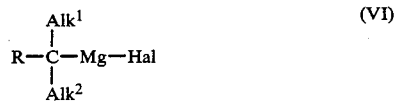

in which

Alk$^1$, Alk$^2$ and R have the abovementioned meaning, and

Hal represents halogen, in the customary manner under the conditions of a Grignard reaction, or by reacting dihalogenoalkanols of the formula

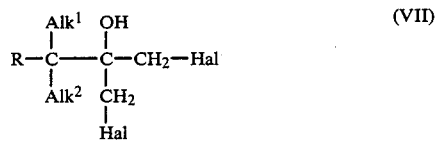

in which

Alk$^1$, Alk$^2$, Hal and R have the abovementioned meaning, with azoles of the formula (III) in the customary manner.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

The compounds of the formula (I) which can be used according to the invention and their acid addition salts display antimicrobial actions, in particular powerful antimycotic actions. They possess a very broad antimycotic action spectrum, especially against dermatophytes and blastomyces as well as biphase fungi, for example against varieties of Candida, such as *Candida albicans*, varieties of Epidermophyton, such as *Epidermophyton floccosum*, varieties of Aspergillus, such as *Aspergillus niger* and *Aspergillus fumigatus*, varieties of Trichophyton, such as *Trichophyton mentagrophytes*, varieties of Microsporon, such as *Microsporon felineum* and varieties of Torulopsis, such as *Torulopsis glabrata*. The listing of these micro-organisms in no way implies a limitation of the germs which can be combated but is only of illustrative character.

Examples which may be mentioned of fields of indication in medicine are: dermatomycoses and systemic mycoses, especially those caused by *Trichophyton mentagrophytes* and other varieties of Trichophyton, varieties of Microsporon, *Epidermophyton floccosum*, blastomyces and biphase fungi as well as moulds.

The present invention includes pharmaceutical formulations which, in addition to non-toxic, inert pharmaceutically suitable excipients, contain one or more active compounds according to the invention, or which consist of one or more active compounds according to the invention, as well as processes for the preparation of these formulations.

The present invention also includes pharmaceutical formulations in dosage units. This means that the formulations are in the form of individual parts, for example tablets, dragees, capsules, pills, suppositories and ampoules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium bicarbonate, (d) solution retarders, for example paraffin, and (f) resorption accelerators, for example cetyl alcohol and glycerol monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the the abovementioned excipients can also be in a micro-encapsulated form.

Suppositories can contain, in addition to the active compound or compounds, the customary water-soluble or water-insoluble excipients, for example polyethylene glycols, fats, for example cacao fat, and higher esters (for example C$_{14}$-alcohol with C$_{16}$-fatty acid), or mixtures of these substances.

Ointments, pastes, creams and gels can contain, in addition to the active compound or compounds, the customary excipients, for example animal and vegetable fats, waxes, paraffins, starches, tragacanth, cellulose derivatives, polyethylene glycols, silicones, bentonites, silica, talc and zinc oxide, or mixtures of these substances.

Powders and sprays can contain, in addition to the active compound or compounds, the customary excipients, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain, in addition to the active compound or compounds, the customary excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerol-formal, tetrahydrofurfuryl alcohol, polyethylene glycols and fatty acid esters of sorbitane, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitane esters, micro-crystalline cellulose, aluminium metahydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95, % by weight of the total mixture.

The abovementioned pharmaceutical formulations can also contain other pharmaceutical active compounds in addition to the active compounds according to the invention.

The abovementioned pharmaceutical formulations are prepared in the customary manner according to known methods, for example by mixing the active compound or compounds with the excipient or excipients.

The present invention also includes the use of the active compounds according to the invention, and of pharmaceutical formulations which contain one or more active compounds according to the invention, in medicine, for the treatment of the abovementioned diseases.

The active compounds or the pharmaceutical formulations can be administered locally, orally, parenterally, intraperitoneally and/or rectally, preferably parenterally, and in particular intravenously. In general, it has proved advantageous to administer the active compound or compounds according to the invention topically, orally or parenterally in total amounts of about 10 to about 300, preferably 50 to 200, mg/kg of body weight every 24 hours, optionally in the forms of several individual administration, in order to achieve the desired results. However, it can be necessary to deviate from the dosages mentioned, and in particular to do so as a function of the species and the body weight of the subject to be treated, the nature and severity of the disease, the nature of the formulation and of the administration and the time or interval over which the administration takes place. Thus it can in some cases suffice to manage with less than the abovementioned amount of active compound, whilst in other cases the abovementioned amount of active compound must be exceeded. The particular optimum dosage required and the type of administration of the active compounds can easily be determined by anyone skilled in the art on the basis of his expert knowledge.

PREPARATION EXAMPLES

Example 1

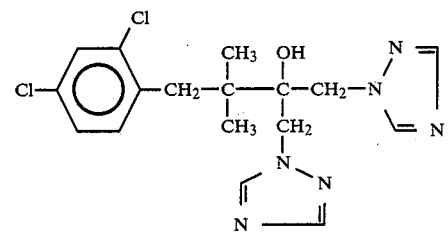

3.7 g (52.5 millimoles) of 1,2,4-triazole are added to a solution of 0.11 g (47 millimoles) of sodium in 30 ml of n-propanol at room temperature, while stirring. The mixture is heated to the reflux temperature and a solution of 15.4 g (47 millimoles) of 2-(2,4-dichlorophenyl-tert.-butyl)-2-(1,2,4-triazol-1-yl-methyl)-oxirane in 20 ml of n-propanol is added. The reaction mixture is heated under reflux for 15 hours and then cooled and poured onto water. The mixture is extracted with methylene chloride and the organic phase is dried over sodium sulphate and concentrated. The residue is purified by column chromatography (silica gel; ethyl acetate:cyclohexane=3:1). 3.5 g (18.8% of theory) of 4-(2,4-dichlorophenyl)-3,3-dimethyl-2-(1,2,4-triazol-1-yl-methyl)-1-(1,2,4-triazol-1-yl)-2-butanol of melting point 126° C. are obtained.

Preparation of the starting material

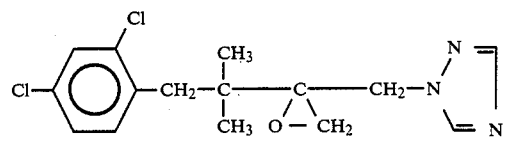

15.7 g (71.2 millimoles) of trimethylsulphoxonium iodide are dissolved in 16 g of dimethylsulphoxide under a nitrogen atmosphere. 9.4 g (71.2 millimoles) of potassium tert.-butylate are added at room temperature, while cooling. The mixture is subsequently stirred for 6 hours and a solution of 20 g (64.1 millimoles) of 4-(2,4-dichlorophenyl)-3,3-dimethyl-1-(1,2,4-triazol-1-yl)-2-butanone in 30 ml of tetrahydrofuran is then added. The reaction mixture is stirred at room temperature for 15 hours and under reflux for 4 hours, cooled and poured onto water. The mixture is extracted with methylene chloride and the organic phase is dried over sodium sulphate and concentrated in vacuo. 15.4 g (73.7% of theory) of 2-(2,4-dichlorophenyl-tert.-butyl)-2-(1,2,4-triazol-1-yl-methyl)-oxirane of refractive index $n_D^{20}$ 1.5539 are obtained.

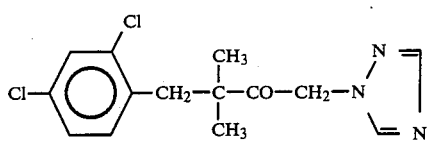

30 g (0.09 mole) of 1-bromo-4-(2,4-dichlorophenyl)-3,3-dimethyl-2-butanone, 12.4 g (0.18 mole) of 1,2,4-triazole and 24.8 g (0.18 mole) of potassium carbonate are heated under reflux in 300 ml of acetone for 6 hours. The mixture is then allowed to cool and is filtered with suction and the mother liquor is concentrated in vacuo. The residue is taken up in methylene chloride and the mixture is washed with water, dried over sodium sulphate and concentrated in vacuo. The residue is recrystallised from diethyl ether. 12.8 g (45.6% of theory) of 4-(2,4-dichlorophenyl)-3,3-dimethyl-1-(1,2,4-triazol-1-yl)-2-butanone of melting point 85° C. are obtained.

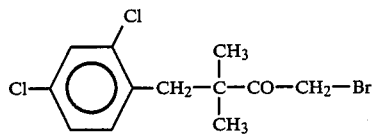

13.4 ml (0.26 mole) of bromine are slowly added dropwise to a solution of 64.5 g (0.26 mole) of 4-(2,4-dichlorophenyl)-3,3-dimethyl-2-butanone in 600 ml of chloroform at room temperature. The reaction solution is subsequently stirred at room temperature for 1 hour. It is then concentrated by distilling off the solvent. 84.3 g (100% of theory) of crude 1-bromo-4-(2,4-dichlorophenyl)-3,3-dimethyl-2-butanone are obtained as an oil, which is further reacted directly.

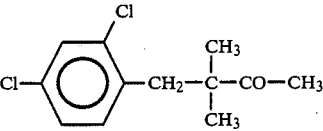

172 g (2 moles) of methyl isopropyl ketone, 391 g (2 moles) of 2,4-dichlorobenzyl chloride, 20 g of tetrabutylammonium bromide and 140 g (2.5 moles) of powdered potassium hydroxide are heated under reflux for 15 hours. The mixture is allowed to cool and water is added. The organic phase is separated off, dried over sodium sulphate and subjected to fractional distillation. 129 g (26.4% of theory) of boiling point 90°–95° C./0.05 mbar are obtained.

The following compounds of the general formula

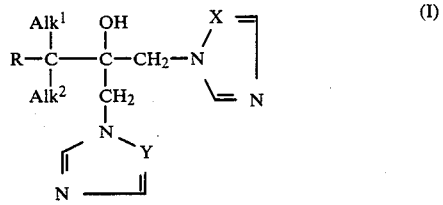

are obtained in a corresponding manner:

| Example No. | R | Alk¹ | Alk² | X | Y | Melting point (°C.) or $n_D^{20}$ |
|---|---|---|---|---|---|---|
| 2 | Cl—⌬—CH₂— | CH₃ | CH₃ | N | N | 132 |
| 3 | CH₃—⌬—CH₂— | CH₃ | CH₃ | N | N | 124 |
| 4 | Cl—⌬—O—CH₂— | CH₃ | CH₃ | N | N | 119–28 |
| 5 | Cl—⌬—S—CH₂— | CH₃ | CH₃ | N | N | 124 |
| 6 | Cl—⌬—O— | CH₃ | CH₃ | N | N | 128 |
| 7 | Cl—⌬—O—CH₂CH₂— | CH₃ | CH₃ | N | N | 1.5460 |

-continued

| Example No. | R | Alk¹ | Alk² | X | Y | Melting point (°C.) or $n_D^{20}$ |
|---|---|---|---|---|---|---|
| 8 | 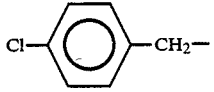 | CH₃ | CH₃ | CH | N | >220(×HCl) |
| 9 | 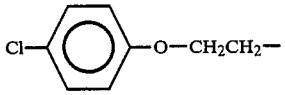 | CH₃ | CH₃ | CH | N | 1.5478 |
| 10 | 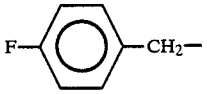 | CH₃ | CH₃ | N | N | 129 |
| 11 | 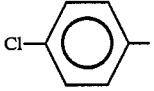 | —C— (cyclobutyl) | | N | N | 78 |
| 12 |  | CH₃ | CH₃ | N | N | 48 |
| 13 | 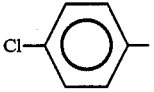 | CH₃ | CH₃ | N | N | 138 |
| 14 | 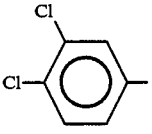 | CH₃ | CH₃ | N | N | 147 |
| 15 | 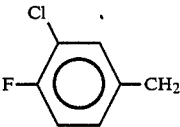 | CH₃ | CH₃ | N | N | 144 |

USE EXAMPLES

Example A

Antimycotic in vitro activity

The in vitro tests were carried out in a series dilution test using germ inocula of on average $5 \times 10^4$ germs/ml of substrate. The nutrient medium used was (a) for dermatophytes and moulds: Sabourand's milieu d'épreuve, and (b) for yeasts: meat extract/glucose broth.

The incubation temperature was 20° C. and the incubation time was 24 to 96 hours for yeasts and 96 hours for dermatophytes and moulds.

In this test, the compounds of preparation examples 1, 2, 3, 5 and 6, in particular, show a good antimycotic action.

TABLE A

Antimycotic in vitro activity

| Active compounds according to preparation example | MIC values in Y/ml of nutrient medium for | | | | |
|---|---|---|---|---|---|
| | Trichophyton mentagr. | Microsporum canis | Candida albicans | Torulopsis glabrata | Aspergillus fumigatus |
| 1 | 1 | 32 | 32 | 64 | 32 |
| 2 | 1 | 4 | 4 | 16 | 4 |
| 3 | 1 | 8 | 16 | 64 | 4 |
| 5 | 1 | 32 | 32 | 64 | 32 |
| 6 | 32 | — | 4 | 16 | 64 |

Example B

Antimycotic in vivo action (oral) in candidosis of mice

Description of the experiment

Mice of the SPF-CF$_1$ type were infected intravenously with 1–2×10$^6$ logarithmically growing Candida cells, suspended in physiological saline solution. The animals were treated orally one hour before and seven hours after the infection, with in each case 10–50 mg/kg of body weight of the products.

Result

Untreated animals died 3 to 6 days after infection. The survival rate on the 6th day after infection was about 5% in the case of untreated animals.

In this test, the compounds of preparation examples, 1, 2, 3, 5, 6 and 8, in particular, show a good to very good action.

Explanation of symbols

+ + + + + = very good action = 90% survivors on the 6th day after infection

+ + + + = good action = 80% survivors on the 6th day after infection

+ + + = action = 60% survivors on the 6th day after infection

+ +32 weak action = 40% survivors on the 6th day after infection

+ = trace of action n.a. = no action

TABLE B

| Antimycotic in vivo activity (oral) in candidosis of mice | |
|---|---|
| Active compound Compounds according to preparation example | Action |
| 1 | + + + + + |
| 2 | + + + + + |
| 3 | + + + + |
| 5 | + + + + |
| 6 | + + + + |
| 8 | + + + + |

EXAMPLE/FORMULATIONS

| (1.) Solution | |
|---|---|
| Active compound according to formula (I) | 10 g |
| Alcohol, pure (96% strength) | 300 g |
| Isopropyl myristate | 526 g |
| | 836 g |

| (2.) Cream | |
|---|---|
| Active compound according to formula (I) | 10 g |
| Arlacel 60 (sorbitan monostearate) | 20 g |
| Tween 60 (polyoxyethylene (20)-sorbitan monstearate) | 15 g |
| Spermaceti, synthetic (mixture of esters of saturated C$_{14}$–C$_{18}$-fatty acids and C$_{14}$–C$_{18}$-fatty alcohols) | 30 g |
| Lanette O (mixture of cetyl alcohol and stearyl alcohol) | 100 g |
| Entanol G (2-octyl-dodecanol) | 135 g |
| Benzyl alcohol | 10 g |
| Water, demineralised | 680 g |
| | 1,000 g |

We claim:

1. A substituted 1,3,-diazolyl-2-propanol of the formula

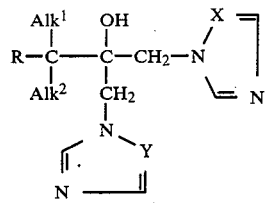

in which

Alk$^1$ represents straight-chain or branched alkyl with 1 to 4 carbon atoms; and Alk$^2$ represents straight-chain or branched alkyl with 1 to 4 carbon atoms; or Alk$^1$ and Alk$^2$ together represent a 3-membered to 7-membered cycloaliphatic ring, X represents a nitrogen atom or the CH group;

Y represents a nitrogen atom or the CH group; and

R represents phenyl, phenylalkyl with 1 to 4 carbon atoms in the alkyl part, phenoxy, phenylthio, phenoxyalkyl with 1 to 4 carbon atoms in the alkyl part, phenylthioalkyl with 1 to 4 carbon atoms in the alkyl part, benzyloxy or benzylthio, each of which is optionally mono-, di- or tri-substituted in the phenyl part by identical or different substituents selected from the group consisting of halogen, alkyl with 1 to 4 carbon atoms, alkoxy and alkylthio with in each case 1 to 4 carbon atoms, halogenoalkyl, halogenoalkoxy and halogenoalkylthio with in each case 1 or 2 carbon atoms and 1 to 5 identical or different halogen atoms, nitro, cyano, hydroxyl, hydroxycarbonyl, alkoxycarbonyl with 1 to 4 carbon atoms in the alkyl part, hydroximinoalkyl with 1 to 4 carbon atoms in the alkyl part, alkoximinoalkyl with 1 to 4 carbon atoms in each alkyl part, and phenyl, phenoxy, benzyl and benzyloxy, each of which is optionally substituted by halogen and/or alkyl with 1 or 2 carbon atoms, or a physiologically acceptable acid addition salt thereof.

2. A compound of the formula (I) in claim 1, in which

Alk$^1$ represents methyl or ethyl; and

Alk$^2$ represents methyl or ethyl; or

Alk$^1$ and Alk$^2$, together with the carbon atom to which they are bonded, represent cyclobutyl, cyclopentyl or cyclohexyl, X represents a nitrogen atom or the CH group;

Y represents a nitrogen atom or the CH group; and

R represents phenyl, benzyl, phenethyl, phenoxy, phenylthio, phenoxymethyl, phenoxyethyl, phenylthiomethyl, phenylthioethyl, benzyloxy or benzylthio, each of which is optionally mono- or di-substituted in the phenyl part by identical or different substituents, substituents which may be mentioned being: fluorine, chlorine, bromine, methyl, isopropyl, tert.-butyl, methoxy, methylthio, trifluoromethyl, trifluoromethoxy, trifluoromethylthio, nitro, cyano, hydroxyl, hydroxycarbonyl, methoxycarbonyl, ethoxycarbonyl, hydroximinomethyl, 1-hydroximinoethyl, methoximinomethyl, 1-methoxyiminoethyl, and phenyl, phenoxy, benzyl and benzyloxy, each of which is optionally substituted by fluorine, chlorine or methyl.

3. A compound of claim 1 which is 4-(2,4-dichlorophenyl)-3,3-dimethyl-2-(1,2,4-triazol-1-yl-methyl)-1-(1,2,4-triazol-1-yl)-2-butanol or a physiologically acceptable acid addition salt thereof.

4. A compound of claim 1 which is 4-(4-chlorophenyl)-3,3-dimethyl-2-(1,2,4-triazol-1-yl-methyl)-1-(1,2,4-triazol-1-yl)-2-butanol or a physiologically acceptable acid addition salt thereof.

5. A compound of claim 1 which is 4-(4-methylphenyl)-3,3-dimethyl-2-(1,2,4-triazol-1-yl-methyl)-1-(1,2,4-triazol-1-yl)-2-butanol or a physiologically acceptable acid addition salt thereof.

6. A compound of claim 1 which is 4-(4-chloro-phenyl-mercapto)-3,3-dimethyl-2-(1,2,4-triazol-1-yl-methyl)-1-(1,2,4-triazol-1-yl)-2-butanol.

7. A compound of claim 1 which is 3-(4-chlorophenoxy)-3,3-dimethyl-2-(1,2,4-triazol-1-yl-methyl)-1-(1,2,4-triazol-1-yl)-2-propanol.

8. A compound of claim 1 which is 4-(4-chlorophenyl)-3,3-dimethyl-2-(1,2,4-triazol-1-yl-methyl)-1-(1,3-diazol-1-yl)-2-butanol.

9. A pharmaceutical composition containing as an active ingredient an antimycotically effective amount of a compound of claim 1 in admixture with an inert pharmaceutical carrier.

10. A pharmaceutical composition containing as an active ingredient an antimycotically effective amount of a compound of claim 1 in the form of a sterile or physiologically isotonic aqueous solution.

11. A composition of claim 9 containing from 0.1 to 99.5% by weight of the said active ingredient.

12. A medicament in dosage unit form comprising an antimycotically effective amount of a compound of claim 1 and an inert pharmaceutical carrier.

13. A medicament of claim 12 in the form of tablets, pills, dragees, capsules, ampoules or suppositories.

14. A method of combatting mycoses in warm-blooded animals which comprises administering to the animals an antimycotically effective amount of a compound of claim 1 either alone or in admixture with a diluent or in the form of a medicament.

15. A method according to claim 14 in which the active compound is administered in an amount of about 10 to about 300 mg per kg body weight per day.

16. A method according to claim 14 in which the active compound is administered orally or parenterally.

* * * * *